United States Patent
Lyons et al.

US006281175B1

(10) Patent No.: US 6,281,175 B1
(45) Date of Patent: *Aug. 28, 2001

(54) MEDICAL EMULSION FOR LUBRICATION AND DELIVERY OF DRUGS

(75) Inventors: Robert T. Lyons, Laguna Hills, CA (US); David H. Dillard, Redmond, WA (US); Bruce Fieggen, Wayne, NJ (US)

(73) Assignees: Scimed Life Systems, Inc., Maple Grove, MN (US); Fresenius Kabi AB, Upsala (SE)

(*) Notice: Subject to any disclaimer, the term of this patent is extended or adjusted under 35 U.S.C. 154(b) by 0 days.

This patent is subject to a terminal disclaimer.

(21) Appl. No.: 09/534,056

(22) Filed: Mar. 24, 2000

Related U.S. Application Data

(63) Continuation-in-part of application No. 08/935,698, filed on Sep. 23, 1997, now Pat. No. 6,054,421.

(51) Int. Cl.[7] .................. C10M 173/00; A61K 9/107

(52) U.S. Cl. .................. 508/491; 508/427; 508/428; 508/513; 514/937; 514/938

(58) Field of Search .................. 514/937, 938; 508/491

(56) References Cited

U.S. PATENT DOCUMENTS

| | | |
|---|---|---|
| 52,301 | 1/1866 | Lester . |
| 1,525,867 | 2/1925 | Koszyczarek . |
| 1,857,501 | 5/1932 | Gallagher . |
| 1,934,100 | 11/1933 | Stiepel . |
| 1,970,902 | 8/1934 | Brunstrum et al. . |
| 2,192,866 | 3/1940 | Musher . |
| 2,210,043 | 8/1940 | Scherr . |
| 2,487,377 | 11/1949 | Roehner et al. . |
| 3,377,276 | 4/1968 | Parker . |
| 4,115,313 | 9/1978 | Lyon et al. . |
| 4,290,910 | 9/1981 | Harada et al. . |
| 4,337,241 | 6/1982 | Ser et al. . |
| 4,567,045 | 1/1986 | Lyons . |
| 4,695,450 | 9/1987 | Bauer et al. . |
| 4,703,062 | 10/1987 | Blackburn et al. . |
| 4,784,845 | 11/1988 | Desai et al. . |
| 4,816,247 | 3/1989 | Desai et al. . |
| 4,920,098 | 4/1990 | Cotter et al. . |
| 4,925,677 | 5/1990 | Feijen . |
| 4,985,250 | 1/1991 | Bee et al. . |
| 4,990,134 | 2/1991 | Auth . |
| 5,010,067 | 4/1991 | Handley et al. . |
| 5,041,292 | 8/1991 | Feijen . |
| 5,089,268 | 2/1992 | Katz . |
| 5,229,023 | 7/1993 | Landis . |
| 5,244,925 | 9/1993 | Wretlind et al. . |
| 5,256,422 | 10/1993 | Albert et al. . |
| 5,258,184 | 11/1993 | Bee et al. . |
| 5,266,359 | 11/1993 | Spielvogel . |
| 5,314,407 | 5/1994 | Auth et al. . |
| 5,331,027 | 7/1994 | Whitbourne . |
| 5,338,471 | 8/1994 | Lal . |
| 5,338,761 | 8/1994 | Nakajima et al. . |
| 5,364,632 | 11/1994 | Benita et al. . |
| 5,393,739 | 2/1995 | Bentz et al. . |
| 5,413,725 | 5/1995 | Lal et al. . |
| 5,427,700 | 6/1995 | Stoffa . |
| 5,427,704 | 6/1995 | Lawate . |
| 5,445,812 | 8/1995 | Gotou . |
| 5,461,037 | 10/1995 | Cotter . |
| 5,472,706 | 12/1995 | Friedman et al. . |
| 5,496,479 | 3/1996 | Videau et al. . |
| 5,554,152 | 9/1996 | Aita et al. . |
| 5,595,965 | 1/1997 | Wiggins . |
| 5,616,342 | 4/1997 | Lyons . |
| 5,618,779 | 4/1997 | Klein et al. . |
| 5,626,873 | 5/1997 | Weiner et al. . |
| 5,645,856 | 7/1997 | Lacy et al. . |
| 5,656,289 | 8/1997 | Cho et al. . |
| 5,658,864 | 8/1997 | Macpherson . |
| 5,658,882 | 8/1997 | Celeste et al. . |
| 5,660,858 | 8/1997 | Parikh et al. . |
| 5,693,337 | 12/1997 | Suzuki et al. . |
| 5,703,022 | 12/1997 | Floyd . |
| 5,728,678 | 3/1998 | Trimbo et al. . |
| 5,736,493 | 4/1998 | Garmier . |
| 5,744,153 | 4/1998 | Yewey et al. . |
| 5,750,142 | 5/1998 | Friedman et al. . |

(List continued on next page.)

FOREIGN PATENT DOCUMENTS

| | | |
|---|---|---|
| 0 268 228 | 5/1988 | (EP) . |
| 0 391 369 | 10/1990 | (EP) . |
| 93/15736 | 7/1993 | (WO) . |
| 99/44523 | 9/1999 | (WO) . |

OTHER PUBLICATIONS

Collins–Gold et al., "Parenteral Emulsions for Drug Delivery," *Advanced Drug Delivery Reviews* 5:189–208 (1990).

*Primary Examiner*—Ellen M. McAvoy
(74) *Attorney, Agent, or Firm*—Christensen O'Connor Johnson Kindness PLLC

(57) ABSTRACT

A medical lubricant suitable for injection into the blood stream of a patient. The lubricant is suitable for use with rotating equipment such as atherectomy drive shafts moving within sheaths and over guide wires and other minimally invasive medical devices introduced into a patient through a catheter like instrument. The lubricant is an oil-in-water emulsion including a surfactant, a co-surfactant, and a pH buffer. The lubricant can further include a cryogenic agent and a pH adjusting agent. One lubricant includes olive oil as an emulsified oil, egg yolk phospholipid as a surfactant, sodium deoxycholate as a co-surfactant, glycerin as a cryogenic agent, L-histidine as a pH buffer, and is pH adjusted using sodium hydroxide. The lubricant can also include a therapeutic agent. The lubricant can withstand freeze/thaw cycles as well as saline dilution, heating, and shear stress without significant creaming, separation, or unacceptable increases in oil droplet size. Compared to saline, the lubricant provides significantly increased lubrication efficiency for rapidly moving parts.

22 Claims, No Drawings

U.S. PATENT DOCUMENTS

| | | |
|---|---|---|
| 5,759,563 | 6/1998 | Yewey et al. . |
| 5,760,020 | 6/1998 | Cotter . |
| 5,801,131 | 9/1998 | Coffey et al. . |
| 5,840,693 | 11/1998 | Eriksson et al. . |
| 5,843,465 | 12/1998 | Lundquist . |
| 5,858,934 | 1/1999 | Wiggins et al. . |
| 5,865,794 | 2/1999 | Castro . |
| 5,885,272 | 3/1999 | Aita et al. . |
| 5,888,947 | 3/1999 | Lambert et al. . |
| 5,902,799 | 5/1999 | Herrmann et al. . |
| 5,925,033 | 7/1999 | Aita et al. . |
| 5,938,632 | 8/1999 | Ellis . |
| 5,948,428 | 9/1999 | Lee et al. . |
| 5,968,059 | 10/1999 | Ellis et al. . |
| 5,993,444 | 11/1999 | Ammar et al. . |
| 6,054,421 | 4/2000 | Lyons et al. . |

MEDICAL EMULSION FOR LUBRICATION AND DELIVERY OF DRUGS

CROSS-REFERENCE TO RELATED APPLICATION

This application is a continuation-in-part of U.S. application Ser. No. 08/935,698, filed Sep. 23, 1997, U.S. Pat. No. 6,054,421.

FIELD OF THE INVENTION

This invention relates to a lubricating composition for use with biomedical devices. More particularly, this invention relates to an injectable emulsion capable of being used within human arteries during a rotational atherectomy procedure that both lubricates the atherectomy device and is capable of acting as a drug carrier.

BACKGROUND OF THE INVENTION

It is well known that, for various reasons, humans can develop a condition in which a type of plaque or hard deposit builds up along the walls of the blood vessels, thereby partially blocking the blood flow and causing severe medical conditions. Several different procedures have been developed for dealing with this situation. One such procedure is rotational atherectomy, in which a rotary mechanical system removes relatively hard intravascular deposits from the walls of human arteries by differentially cutting away the inelastic, hardened deposits while sparing the soft, elastic tissue of the inner lining of the human blood vessels. The seminal patent that discloses a device for performing this procedure is U.S. Pat. No. 4,990,134 (Auth) entitled "TRANSLUMINAL MICRODISSECTION DEVICE", the disclosure of which is incorporated herein by reference.

In the commercially available device described in U.S. Pat. No. 4,990,134, known as the Rotablator®, an ellipsoidal burr coated with tiny diamond chips is rotated at a speed of at least approximately 155,000 revolutions per minute. The burr is connected to a drive motor capable of high speed rotation via a hollow, flexible, helically-wound drive shaft, and is routed through the blood vessel over a narrow guide wire that extends through the central bore of the burr and its drive shaft. When this device is operated, the burr preferentially cuts hard, inelastic material (plaque) while sparing soft, elastic material (tissue) and generates microscopic debris fragments that are sufficiently small in size so as to pass through even the narrowest vascular channels (capillary beds) without clogging them.

This Rotablator® atherectomy device, as well as any other microdissection device that involves rotational ablation, necessarily generates thermal energy during its rotation. For this reason, as disclosed in U.S. Pat. No. 4,990,134, a biocompatible saline solution is infused through a plastic sheath within which the drive shaft rotates, to cool the sliding interface during operation.

In addition to performing a cooling function, some lubrication is needed to prevent wear caused by rotational friction between the guide wire and the drive shaft or between the drive shaft and the plastic sheath. The major factors that affect wear in this type of rotational contact are load, temperature, surface speed, surface finish, surface hardness, contact area, time, and the type, amount and viscosity of the lubricant.

During extended operation of the device, however, additional lubrication should be provided to sustain the performance of the guide wire, the drive shaft and the sheath. Such a lubricant, if infused through the device from outside the patient's body, must of course, be non-toxic and safe for arterial use. In addition, to be effective in use with the Rotablator® advancer/guide wire system, the lubricant should be able to withstand shear stresses at 50° C. and should not promote the. agglomeration of ablated plaque particles.

Injectable oil-in-water emulsions are currently being used for two clinical applications. The first is for parenteral or intravenous nutrition, as a source of fat calories and essential fatty acids. Examples include Intralipid®, available from Pharmacia and Upjohn and Liposyn®, available from Abbott Laboratories. Emulsions are also being used as a vehicle for poorly water-soluble lipophilic drugs that cannot be injected directly. Examples include Diprivan®, containing the anesthetic drug propofol, and Diazemuls®, containing the drug diazepam.

Lipid emulsions are inherently unstable. No commercially available lipid emulsion is stable following dilution in physiological (0.9% w/v) salt solution. This instability is manifested by formation of large droplets of non-emulsified oil on the surface as well as by a shift in droplet size distribution towards much larger diameters. Such changes often occur within the first hour following dilution in saline and are accelerated by heating or by applying any shear force. The relatively low pH and high ionic strength of saline contributes to this effect.

Commercial lipid emulsions separate into oil and water layers upon thawing after storage at freezing temperatures. For this reason, special care must be taken when shipping in winter through geographic areas having below freezing temperatures. It is preferred that the lubricant be an emulsion which is stable in saline and stable upon freezing with subsequent thawing. The present invention meets these needs and overcomes other deficiencies in the prior art.

What would be desirable is an improved, pharmacologically compatible medical lubricant that is capable of delivering therapeutic agents to target locations within the body. What has not been provided in the prior art is an injectable medical lubricant suitable for lubricating rotating and otherwise moving medical devices, where the lubricant can optionally act as a carrier for therapeutic agents to thereby yield a therapeutic effect to a treatment site in the body.

SUMMARY OF THE INVENTION

The present invention includes a medical lubricant suitable for injection into a patient. The lubricant is an oil-in-water emulsion including an oil, a surfactant, a co-surfactant and water. The lubricant preferably also includes a cryogenic agent, a pH buffer, and a preservative. The lipid emulsion preferably has a mean particle or droplet diameter of less then 1 micrometer, most preferably less than about 0.5 micrometer. The lubricant can be subjected to substantial shear by a rotating member, exhibits a commercially acceptable shelf life during storage under ambient temperatures, and is able to withstand freeze-thaw cycles without substantial degradation. The lubricant can be diluted in physiological saline for injection and maintains suitable emulsion droplet size after such dilution.

The oil can be a vegetable oil or a medium chain triglyceride. The preferred oil is refined olive oil, which preferably comprises mostly mono-unsaturated oleic acid. The oil can lubricate medical devices such as rotating drive shafts in atherectomy devices, thereby reducing wear on moving parts. A mean droplet size of less than about 1 micrometer allows injection into the bloodstream and subsequent absorption by the body without ill effect. The emulsion most preferably includes about 20 g refined olive oil per 100 mL emulsion.

The surfactant can be a phospholipid, preferably purified egg yolk phospholipids. The surfactant stabilizes the oil droplets dispersed in the continuous aqueous phase. The present invention preferably includes about 1.2 g egg yolk phospholipids per 100 mL emulsion.

The co-surfactant can be a salt of a bile acid, most preferably sodium deoxycholate. The co-surfactant significantly improves droplet stability after saline dilution, heating, and exposure to high shear forces. Droplet stability includes the resistance to formation of larger droplets, creaming, and formation of a separate oil layer. Bile salt, acting in conjunction with glycerin, provides improved freeze-thaw stability. Applicants believe the bile salt also improves lubricity by acting as a wetting agent, improving the coating of moving metal parts. The present invention most preferably includes about 0.4 g bile salt per 100 mL emulsion.

The cryogenic agent can be refined propylene glycol or glycerin, preferably glycerin. Glycerin also provides improved lubricity. The present invention preferably includes about 10 g glycerin per 100 mL emulsion.

The pH buffer imparts improved droplet stability in a saline diluent. Any physiological pH buffer may be used. When the pH buffer is an amino acid buffer said amino acid buffer usually has a concentration of less than 0.20 g/100 mL emulsion. The amino acid buffer is most preferably L-histidine in a concentration of about 0.16 g per 100 mL emulsion.

The preservative is preferably a heavy metal chelator such as disodium EDTA. EDTA, and the histidine buffer, serve as antioxidants, protecting unsaturated fatty acids found in egg yolk phospholipids. The antioxidants provide an extended shelf life for the emulsion at room temperature and inhibit peroxide formation during clinical use. Disodium EDTA is preferably present in about 0.014 g per 100 mL emulsion.

The emulsion preferably has the pH adjusted to between about 8.3 and 8.8 with a base such as sodium hydroxide. This pH range optimizes the emulsion stability in the presence of non-buffered saline, which is slightly acidic. Sodium hydroxide can be present in about 3.0 mEq per liter of emulsion.

An emulsion according to the present invention can be prepared by combining refined olive oil, 1.2% egg yolk phospholipid, 0.16% L-histidine (10 mM), 0.014% disodium EDTA (0.5 mM), and water, followed by ultrasonic processing for about 15 minutes. The emulsion can also be prepared using high pressure homogenization techniques well known to those skilled in the art.

In use, the emulsion can be stored for at least eighteen (18) months, preferably twenty-four (24) months at room temperature. The emulsion can be stored frozen at −F30° C., and then thawed without causing significant changes in droplet size distribution. The emulsion can be added to normal, unbuffered 0.9% saline solution. One anticipated use is injection of the emulsion into an IV bag of saline, thereby diluting the emulsion. The diluted emulsion can be infused from the IV bag through a catheter tube housing a rotating member such as an atherectomy drive shaft or an ultrasonic probe drive shaft. The emulsion serves to lubricate the moving parts and can thereafter enter the blood stream of a patient without ill effect.

In certain embodiments of the invention, the above described medical lubricant additionally includes one or more therapeutic agents to thereby provide a therapeutic effect to a treatment site in the body. One or more of the therapeutic agents may include a genetic material encoding a therapeutic agent, a non-genetic therapeutic material, proteins or cells that produce a therapeutic effect. The choice of therapeutic agent will depend on the application. In one embodiment where the lubricant is used in conjunction with an atherectomy device, one or more of the therapeutic agents inhibits cell proliferation and provides an anti-restenosis effect. In other embodiments where the lubricant is used in conjunction with a transmyocardial revascularization (TMR) device or percutaneous myocardial revascularization (PMR) device, one or more of the therapeutic agents promotes angiogenesis.

In yet another aspect of the invention, a method is provided for lubricating an intravascular device. The inventive method involves first preparing a patient for a medical procedure and then inserting into the patient a medical device that is in need of lubrication. A medical oil emulsion lubricant is infused into the patient during the insertion and/or operation of the medical device. The medical oil emulsion lubricant contains olive oil, an egg yolk phospholipid, a bile salt, an amino acid buffer and a desired therapeutic agent. In one embodiment of the method the medical procedure is atherectomy and the medical device is an intravascular device that is capable of differentially removing intravascular deposits from the walls of an artery. During the atherectomy procedure the therapeutic agent present in the medical oil emulsion lubricant usually contains a cell proliferation inhibitor that provides an anti-restenosis effect. In another embodiment of the lubrication method, the medical procedure is myocardial revascularization and the medical device is a myocardial revascularization device. During the myocardial revascularization procedure it is usual to include in the medical lubricant a therapeutic agent that promotes angiogenesis.

DETAILED DESCRIPTION

In a preferred embodiment of the invention, the oil-in-water emulsion lubricant comprises a mixture of water, oil, a surfactant, a co-surfactant, a phospholipid, a cryogenic agent, a pH buffer and a preservative.

Preferably the oil used in the lipid emulsion lubricant is a liquid at room temperature, most preferably olive oil.

Chemically, olive oil contains mostly mono-unsaturated oleic acid. Different oil bases, such as either soybean oil, which contains a mixture of polyunsaturated fatty acids, mainly $C_{14}$ $C_{16}$, and $C_{18}$, or medium chain triglycerides (MCT) may also be used, especially with varying concentrations of the other ingredients and with different surfactants. Almond oil, coconut oil, corn oil, cotton seed oil, marine oil, palm kernel oil, peanut oil, safflower oil, sesame oil, sunflower oil, and physical or interesterified mixtures thereof can also be used. These other oil bases, however, are not as effective as olive oil. Quite surprisingly, we found that olive oil emulsions lubricate better than soybean oil emulsions. The lubricant reduces wear on moving components. In a preferred embodiment of the invention, the concentration of olive oil in the lubricant is from about 5 to about 40 g/100 mL emulsion, more preferably about 15 to about 25 g/100 mL emulsion, and is most preferably about 20 g/100 mL emulsion.

An emulsion is a dispersion of one immiscible liquid within another, commonly oil-in-water. An emulsifier is a surface active agent designed to coat and stabilize the dispersed droplets against coalescence. However, in certain formulations, this dispersion is insufficiently stabilized by the primary emulsifier which is typically added at concentrations of about 1–5% w/v. In such cases, a second surface active agent, known as a co-surfactant, may be added. A co-surfactant is typically used at a fractional concentration of the primary emulsifier, e.g., 0.1–1.0%. In principle, co-surfactants are added to accomplish specific tasks such as enhancing electrostatic surface charge on the dispersed droplets or strengthening the interfacial film between oil and water. In reality, it is quite difficult to predict in advance which co-surfactant, if any, will stabilize a novel emulsion formulation under specific environmental conditions.

A primary emulsifier in the lipid emulsion lubricant could, for example, be selected from a group of phospholipids such as soy bean or egg yolk phospholipids. A preferred phospholipid is egg yolk phospholipid, preferably present in a concentration of about 0.3 to about 3 g/100 mL emulsion, more preferably about 0.6 to about 1.8 g/100 mL emulsion, most preferably about 1.2 g/00 mL emulsion.

The co-surfactant could be, for example, PEG-400 (polyethylene glycol), Pluronic F68 (a nonionic, polyoxethylene-polyoxypropylene block copolymer, BASF), dimyristyl phosphatidyl glycerin (DMPG), or the salt of a bile acid. When PEG-400 is used, it can be present at about 5% weight/volume. When Pluronic F68 is used, it can be present at about 1% weight/volume. Preferably, the co-surfactant is the salt of a bile acid such as cholic acid, deoxycholic acid, taurocholic acid or mixtures thereof. Most preferably, the co-surfactant is sodium deoxycholate, as it is somewhat more effective in reducing wear than DMPG. In the present invention, the superiority of sodium deoxycholate over other tested co-surfactants was unexpected and unpredicted. In a preferred embodiment, sodium deoxycholate is present at a concentration of about 0.04 to about 4 g/100 mL emulsion more preferably about 0.2 to about 0.8 g/100 mL emulsion, most preferably about 0.4 g/100 mL emulsion.

A preferred cryogenic agent is refined propylene glycol or glycerin, most preferably glycerin. Glycerin serves to provide freeze tolerance and improves the overall lubricating properties of the emulsion. Glycerin is preferably present at a concentration of about 1 to about 30 g/100 mL emulsion, more preferably about 2 to about 20 g/100 mL emulsion, most preferably about 10 g/100 mL emulsion.

A preferred pH buffer is an amino acid buffer, for example, alanine, aspartic acid, glycine, histidine, isoleucine, leucine, methionine, phenylalanine, proline, serine, valine or mixtures thereof. Often the amino acid buffer is present at a concentration lower than about 0.20 g/100 mL. A preferred amino acid buffer is histidine. Histidine contributes significant pH buffering capacity in the critical pH 6 to 8 range, having a $PK_a$ of about 6.0. This pH buffering contributes to emulsion stability after dilution in saline. In addition, histidine serves as an antioxidant, specifically a hydroxy radical scavenger. Histidine is preferably present at a concentration of about 0.01 to about 1 g100 mL emulsion, more preferably about 0.05 to about 0.3 g/100 mL emulsion, most preferably about 0.16 g/100 mL emulsion.

A preferred preservative is a heavy metal chelator such as disodium EDTA. The combination of EDTA and histidine serves as a potent antioxidant to protect unsaturated fatty acids found in egg yolk phospholipids. This antioxidant system serves both to protect the emulsion in the bottle during prolonged storage at room temperature as well as to inhibit peroxide formation during clinical use. Disodium EDTA is preferably present at a concentration of about 0.001 to about 0.1 g/100 mL emulsion, more preferably about 0.01 to about 0.05 g/100 mL emulsion, most preferably about 0.014 g/100 mL emulsion.

Finally, sodium hydroxide can be added to titrate the emulsion to a final pH of about 8.3 to about 8.8. This pH range is chosen to optimize emulsion stability in the presence of non-buffered saline which is slightly acidic.

In order to manufacture the present invention, a mixture of water-for-injection with the ingredients listed above in the amounts described can be passed through a high pressure homogenizer. The resulting mixture is an opaque white, milky liquid that is a suspension of small oil droplets in water, with a normal droplet size distribution. The droplet size has a mean of about 0.4 μm and a maximum of about 4 μm. The distribution includes 90% of droplets less than about 0.65 μm and less than 0.5% of droplets greater than 1 μm. Even after experiencing high shear, all droplets remain less than about 5 μm.

The lubricant is to be shipped in sterile vials and injected into a sterile saline intravenous (IV) bag prior to use. During a rotational atherectomy procedure, the lubricant can be infused through the catheter of a Rotablator® system and then into the coronary artery. Because the present invention is safe for parenteral use, it is a potential lubricant for any device operating inside the human body. Examples of this are: interoperative milk into which endoscopic equipment is dipped before placement into the human body; coating for sutures in order to reduce friction; lubricant for heart valves in order to ease placement during surgery; lubricant for ultrasonic catheters; and lubricant for other future devices that employ swiftly-moving parts within the body. In addition, the medical lubricants of the present invention can also be used during placement in the body of catheter like tubes such as are used, for example during atherectomy, transmyocardial revascularization, angioplasty and the like. The medical lubricant emulsions facilitate the advancement of the catheter in a blood vessel by lubrication of the contact zone between the catheter and the blood vessel. The medical lubricants of the invention can similarly be used to ease the placement and advancement of medical devices through the catheter to a site of use in the body in addition to lubricating moving parts within the medical device. The inventive medical lubricants can also contain therapeutic agents that are introduced via a catheter into the body to a specific target location. The medical lubricant emulsion can be infused into the body through a catheter or through a medical device that is located inside a guide catheter.

Depending on the application, the medical lubricant optionally includes one or more therapeutic agents such as a genetic material, a non-genetic therapeutic material, or cells.

Examples of therapeutic agents used in accordance with the invention include, but are not limited to: anti-thrombogenic agents such as heparin, heparin derivatives, urokinase, and PPack (dextro-phenylalanine-proline-arginine-chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Argchloromethylketone, an arginine-glycine-aspartic acid (RGD) peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators of genes encoding vascular cell growth promoter proteins, and translational activators of mRNAs encoding vascular cell growth promoter proteins; vascular cell growth inhibitors such as growth factor inhibitors, growth factor receptor antagonists, transcriptional repressors of genes encoding vascular cell growth inhibitors, translational repressors of mRNAs encoding vascular cell growth inhibitors, DNA replication inhibitors, vascular cell growth inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

In embodiments in which the therapeutic agent includes a substantially purified genetic material, useful polynucleotide sequences include, for example, DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides useful in the invention can also code for therapeutic polypeptides. A therapeutic polypeptide is understood to be any substantially purified translation product of a polynucleotide regardless of size, and whether glycosylated or not. Therapeutic polypeptides include, as a primary example, those polypeptides that can compensate for a defective or deficient species in an animal, or those that act through toxic effects to limit or remove harmful cells from the body. In addition, the polypeptides or proteins that can be incorporated into the coating material of the present invention, or whose DNA can be incorporated, include without limitation, angiogenic factors including acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CD inhibitors; thymidine kinase ("TK") and other agents useful for interfering with cell proliferation, including agents for treating malignancies. Still other useful factors, which can be provided as polypeptides or as DNA encoding these polypeptides, include the family of bone morphogenic proteins ("BMPs") See, for example, U.S. Pat. Nos. 5,948, 428, 5,658,882 and 5,393,739. The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

In other embodiments, one or more of the therapeutic agents include cells. The therapeutic cells can be of human origin (autologous or allogeneic) or from an animal source (xenogeneic). The cells may be genetically engineered if desired to deliver proteins of interest at the site of cell deposition. The medical lubricant is preferably formulated as needed to maintain cell function and viability.

In a preferred embodiment, the medical lubricant is used in conjunction with an atherectomy device and includes a therapeutic agent that inhibits restenosis. In this embodiment, the therapeutic agent inhibits smooth muscle cell proliferation and comprises a therapeutic agent such as paclitaxel.

In another embodiment, the medical lubricant is used in conjunction with a mechanical transmyocardial revascularization procedure, such as described in U.S. Pat. No. 5,968,059, which is incorporated herein by reference. The medical lubricants of the present invention are used to lubricate the moving parts of the mechanical transmyocardial revascularization device during performance of the procedure. Alternatively, the inventive medical emulsions can be used in conjunction with other transmyocardial and percutaneous myocardial revascularization devices that utilize a variety of different means to introduce myocardial wounds, such as, for example, a laser transmyocardial revascularization device (U.S. Pat. Nos. 5,925,033 and 5,885,272), a radio frequency transmyocardial revascularization device (U.S. Pat. No. 5,938,632), a cyro transmyocardial revascularization device (U.S. Pat. No. 5,993,444) or an electrode percutaneous myocardial revascularization device (PCT patent application No. PCT/US99/04942). Introduction of a medical lubricant of the present invention during a myocardial revascularization procedure may be desirable to lubricate movement of the myocardial ablation device through a tubular delivery catheter as well as during placement of the catheter itself into the patient. In this embodiment of the invention, the medical lubricant preferably comprises a therapeutic agent that promotes angiogenesis such as growth factors, vascular endothelial growth factors, and DNA that encodes these growth factors.

Experimental Results

Sample Preparation

Four one-liter lots of 20% olive oil emulsion were prepared, with each 100 mL of emulsion containing: 20.0 g olive oil, 1.2 g egg yolk phospholipid (a surfactant), 0.40 g sodium deoxycholate (a bile salt co-surfactant), 0.16 g L-histidine (an amino acid pH buffer), and 0.014 g disodium EDTA (a preservative). 3.0 mEq/L NaOH was also added to adjust pH. The four lots varied only in glycerin content (a cryogenic agent) in the amounts specified in Table 1. Intralipid, a commercially available lipid emulsion for parenteral nutrition, is included in Table 1 for comparison. Intralipid 20% contains 20% w/v soybean oil, egg yolk phospholipids, glycerin, sodium hydroxide, and water for injection (WFI).

TABLE 1

Glycerin Concentration, Osmolality and Zeta Potential

| Lot Number | Glycerin Conc., Grams/100 mL | Osmolality, mOsm/kg | Zeta Potential, mv |
|---|---|---|---|
| Intralipid 20% | 2.25 | 350* | −38 |
| HT-049 | 1.6 | 280 | −46 |
| HT-050 | 10.0 | 300 | −48 |

TABLE 1-continued

Glycerin Concentration, Osmolality and Zeta Potential

| Lot Number | Glycerin Conc., Grams/100 mL | Osmolality, mOsm/kg | Zeta Potential, mv |
|---|---|---|---|
| HT-051 | 20.0 | 322 | −44 |
| HT-052 | 30.0 | 346 | −40 |

*undiluted sample

High glycerin concentrations are expected to elevate osmolality and depress the freezing point. The original formulation was designed with 1.6% glycerin to produce an isotonic product, having about 280–320 mOsm/kg. As osmolality could not be measured directly in higher concentration glycerin samples using the freezing. point depression method, osmolality was measured after a 1:50 dilution in 0.9% saline. This dilution was chosen to represent expected clinical practice. The osmolality of the Intralipid was measured on an undiluted sample.

The Zeta potential or net surface charge is an important determinant of stability in colloidal systems. Zeta was calculated from microelectrophoretic mobility in 5 mM Hepes buffer at pH 8.0 using a laser light scattering detection system (Malvern ZetaSizer). Control (non-frozen) samples were used. As can be seen in Table 1, Zeta potential was most negative at about 10% glycerin concentration.

Visual Inspection

At least three separate bottles from each lot were visually inspected for homogeneity and surface oil. Inspections were performed on initial samples about one week after sterilization and on samples that had been subjected to freeze/thaw and shipping. "Creaming" refers to the rapid floatation (e.g., within an hour) of large, emulsified oil droplets formed either by coalescence or by aggregation of smaller emulsified droplets. In contrast, surface oil ("free oil") droplets are not emulsified. The results of visual inspection are summarized in Table 2. As can be seen in Table 2, Lot HT-050, having 10% glycerin, had no surface oil and no creaming, either initially or after the freeze/thaw cycle.

TABLE 2

Visual Examination

| Lot No. | Initial (non-frozen) | Post Freeze/Thaw (all temperatures) |
|---|---|---|
| HT-049 | no surface oil; no creamimg | no surface oil; rapid formation of cream layer |
| HT-050 | no surface oil; no creamimg | no surface oil; no creamimg |
| HT-051 | a few oil droplets (≦1 mm); no creaming | a few oil droplets (≦1 mm); no creaming |
| HT-052 | no surface oil; no creamimg | no surface oil; no creamimg |

Freeze/Thaw and Stress Testing

Measurements of pH and droplet size were performed on triplicate samples from each lot. Test samples were subjected to freeze/thaw and shipping. Control samples were subjected to no freezing, only shipping. Both control and freeze/thaw samples were subjected to a saline/heat/shear stress test. This test involves a 1:20 dilution in 0.9% saline, followed by heating in a 40 degree C water bath for 5 minutes, and ending with 3 minute high-shear processing by a rotor-stator device (Ultra Turrax, 20,500 rpm) at 40° C. Due to significant deterioration (creaming),. freeze/thaw samples from Lot HT-049 (1.6% glycerin) were not subjected to this test. Some of the data for Intralipid 20% and Lot HT-050 (10% glycerin) are summarized in Table 3.

Table 3 contains the results: pH (before and after freeze/thaw for Lot HT-050); pH after dilution/heat/shear; mean droplet diameter before and after dilution/heat/shear; droplet diameter for which 90% of the droplets have a smaller diameter before and after dilution/heat/shear; droplet diameter for which 100% of the droplets have a smaller diameter before and after dilution/heat/shear; and the percent of droplets having a droplet diameter greater than 1 micrometer before and after dilution/heat/shear.

Inspection of Table 3 shows a significant increase in droplet diameter after dilution/heat/shear stress for Intralipid 20%. As previously discussed, freeze/thaw of Intralipid 20% results in phase separation. Lot HT-050 (10% glycerin) in the control (before freeze/thaw) shows a very slight increase in droplet diameter at the 90th percentile and a maximum droplet size of 4.30 micrometers due to dilution/heat/shear. This compares with an Intralipid increase from 0.80 to 1.23 micrometers droplet diameter at the 90th percentile and maximum droplet size of 12.2 micrometers due to dilution/hear/shear. Freeze/thaw had an insignificant effect on droplet size for the Lot HT-050 sample. Freeze/thaw also had no significant change on the effects of dilution/heat/shear on the HT-050 sample after thawing.

TABLE 3

Effects of Freeze/Thaw and Heat/Shear on 20% Olive Oil Emulsions

| Lot No./ Storage Condition | pH | Heat/ Shear pH | Mean Dia, μm | Heat/ Shear Mean Dia | 90% <μm | Heat/ Shear 90% <μm | 100% <μm | Heat/ Shear 100% <μm | % <1 μm | Heat/ Shear % <1 μm |
|---|---|---|---|---|---|---|---|---|---|---|
| Intralipid 200%/Control | 7.85 | 6.70 | 0.49 | 0.67 | 0.80 | 1.23 | 3.49 | 12.2 | 4.6 | 13.9 |
| 50/Control | 8.63 | 7.42 | .040 | .042 | 0.61 | 0.65 | 1.51 | 4.30 | 0.50 | 3.4 |
| 50/Frozen @ −30° C. | 8.64 | 7.54 | 0.40 | 0.41 | 0.61 | 0.64 | 1.51 | 4.30 | 0.50 | 2.6 |

Phase-Contrast Microscopy

The samples were also observed under phase-contrast microscopy. Freeze/thaw samples from HT-049 (1.6% glycerin) showed a very large number of coalesced and aggregated oil droplets. In contrast, all elevated glycerin samples, HT-050 (10% glycerin), HT-051 (20% glycerin), and HT-052 (30% glycerin) had a very uniform, clean appearance with no large droplets. Samples were also observed after the saline/heat/shear stress test. Samples from all olive oil lots looked excellent, while the Intralipid samples showed many large coalesced droplets. These observations are consistent with the drop size distribution data shown in Table 3.

Sample Test Summary

The addition of glycerin at 10% weight/volume appears sufficient to protect the olive oil emulsions from freeze/thaw damage for at least 48 hours, even at minus 30 degrees C. In this respect, no advantages were seen with higher concentrations of glycerin. The presence of elevated glycerin concentration had no significant effect on product appearance, pH, drop size distribution or Zeta potential. In contrast, the 1.6% glycerin sample (ET-049) exhibited severe creaming following freeze/thaw. The complete preservation of emulsion quality during freeze/thaw using only 10% w/v glycerin (e.g., lot #HT-50) was quite surprising and unexpected. Since samples stored at −30° C. appear to be frozen solid, glycerin is not acting as a simple antifreeze agent. Cryopreservation must be occurring by an action at the oil-water interface of the dispersed droplets, i.e., in the phospholipid monolayer.

The addition of each 10% of glycerin, after a 50-fold dilution in 0.9% saline, adds about a 20 mOsm/kg increment in osmolality. Thus, even a 30% glycerin emulsion has a diluted osmolality no higher than undiluted Intralipid 20%. Therefore no tonicity problems are expected in clinical applications.

Utility

The utility of the invention was tested using the Rotoblator system. This system rotates a 135 cm stainless steel drive coil with an attached diamond coated burr over a 0.009 inch diameter stainless steel guide wire at 180,000 rpm. The system in current use is lubricated during startup with a thin film of HYSTRENE on the guide wire and throughout the operation by a continuous infusion of normal saline. This allows for efficient operation for only limited duration, as the lubricant washes away and is not replenished, therefore the performance can start to degrade as the device starts operating. Performance degradation can take the form of loss of speed, heat build-up, guide wire wear, drive coil wear, burr wear and reduced axial mobility.

Optimally, for use with the Rotoblater Advancer/guide wire system, the lubricant should withstand high shear stress at 50° C. without emulsion degradation. All emulsion droplets should remain less than 5 micrometers in diameter, even after shear stress associated with use of this device. In addition, a mixture of the emulsion in saline should remain stable after overnight storage at room temperature and be non-toxic.

Wear and Speed Stability Test

Lubricants were tested using the Rotoblater advancer. An advancer having a 1.75 mm burr was passed through a PTFE tube with a 2.2 mm ID which is wrapped over a pair of mandrels to create a fixed "S" shaped path. The guide wire distal end is placed about 2 inches past the burr and the fixture immersed in a 37° C. waterbath and run for 5 minutes. The lubricants tested included both normal saline and saline mixed with 20 cc per liter of the olive oil emulsion. The advancer speed was recorded and the wear scars on the guide wire wear measured with a Laser Micrometer. With saline alone, average wear was 0.0048 inch compared with only 0.0001 inch wear for saline with the emulsion added. With saline alone, the average speed change was a decrease of 13877 rpm, compared with an average increase of 79 rpm for saline with the emulsion added. Thus, both guide wire wear and speed stability improved with the emulsion added.

Tortuous Advance Force Test

Another series of tests was performed, similar to the previous study but having a more tortuous path, to simulate the path of a coronary vessel. The burr was advanced and retracted over an "S" shaped bend throughout the 5 minute test. The test measured the force required to advance and retract the burr, the advancer speed, and the fluid temperature downstream of the burr in the PTFE tube. With saline alone, the rpm decreased by 13,000 rpm compared with an increase of 800 rpm for saline with emulsion. With saline alone, the peak fluid temperature was 58° C. compared with 47.5° C. for saline with emulsion. With saline alone, 170 gm of force was required at the peak to advance the device, compared with 120 gm for saline with emulsion. Thus, the emulsion provided improved lubrication over saline alone.

Comparison with Other Lipid Emulsions

Another study was performed using stainless steel rods with surface speeds and pressures similar to those found in the Rotoblater. A series of emulsions of olive oil and Intralipid was tested for wear resistance and emulsion stability. The average wear scars using Intralipid were 64 millionths of an inch +/−16, compared to only 5 millionths of an inch +/−11 for olive oil emulsions. Furthermore, the olive oil emulsion showed insignificant post shear changes in droplet size distribution, the mean droplet diameter remaining about 0.4 micrometers. In distinct contrast, the Intralipid lubricant showed a dramatic degradation in the emulsion, including an increase in maximum droplet diameter to about 10 micrometers, an increase in mean droplet diameter to about 0.8 micrometers, an increase in 90th percentile droplet diameter from about 0.8 micrometers to about 2 micrometers, and a bimodal distribution in droplet diameter, having a second peak at about 2 micrometers.

Oil Emulsions Comparison Tests

A series of oil emulsion samples was prepared, all containing 20% weight/volume oil, 1.2% egg yolk phospholipid, 0.16% L-histidine (10 mM), and 0.014% disodium EDTA (0.5 mM). Additional excipients in each sample are indicated in Table 4. Emulsions were prepared by ultrasonic processing (Sonics and Materials Inc., 13 mm horn, 200 mL sample volume, and 80% power for 15 minutes at 50% duty cycle). Drop size distribution was determined by laser light scattering (Malvern MasterSizer). Stainless steel wear testing was expressed as a ratio of stainless steel volume lost with a saline control divided by the volume lost with the test emulsion. Higher ratios indicate less steel lost and therefore better lubrication.

TABLE 4

Olive Oil-in-Water Emulsion is Most Effective for Lubrication

| Prep No. | Oil Phase, 20% w/v | Aqueous Additive % w/v | Sterile pH | Mean Dia, μm | % >1 μm | Stainless Steel Wear, Saline Emulsion |
|---|---|---|---|---|---|---|
| 1 | MCT | None | 8.14 | 1.10 | 18.4 | 1.09 |
| 2 | MCT | Glycerin 2.25% | 8.25 | 0.95 | 16.8 | 1.56 |
| 3 | MCT | PEG-400, 5.0% | 8.21 | 0.87 | 18.8 | 0.95 |
| 4 | MCT | Pluronic F68, 1.0% | 8.24 | 0.49 | 4.2 | 1.88 |
| 10 | 15% MCT 5% Castor Oil | None | 8.11 | 0.75 | 18.4 | 2.53 |
| 6 | Olive | None | 8.20 | 0.65 | 13.0 | 23.71 |
| 9 | SBO | None | 8.25 | 0.81 | 25.6 | 7.12 |

As can be seen from inspection of Table 4, there was a dramatic and unexpected advantage with respect to lubrication efficiency using purified olive oil (Croda) as the emulsified lipid phase versus other oils such as MCT (medium chain triglycerides). Other studies (not shown) confirmed the superiority of olive oil.

Co-surfactant Emulsion Stability Test

In order to be useful as a lubricant emulsion, the injectable product must be stable for several hours after dilution in unbuffered, normal, 0.9% saline solution. Therefore, a series of samples having various aqueous co-surfactants was tested in a 20% olive oil emulsion. The samples included a control having no co-surfactant, PEG-400 added at 5%, Pluronic F68 (nonionic block copolymer) added at 1%, sodium deoxycholate (a bile salt) added at 0.2%, and Intralipid 20%. The emulsions were diluted 1:20 in 0.9% saline and allowed to stand overnight at room temperature. Emulision quality was scored by monitoring the formation of large droplets (%>1 micrometer) using a laser light scattering instrument. In decreasing order of the percentage of droplets having a diameter greater than 1 micrometer, Intralipid had 60% Pluronic F68 42%, PEG-400 37%, control 25%, and deoxycholate 6%. From several experiments such as this, we concluded that the use of deoxycholate as a co-surfactant best protects this olive oil emulsion following saline dilution.

Diluted Intralipid Droplet Size Tests

Intralipid was evaluated for use as a lubricant in a stainless steel wear test. Intralipid was evaluated after dilution in Water For Injection (WFI), after dilution 1:20 in saline, and after dilution in saline with heat/shear stress. The initial Intralipid mean droplet diameter after dilution in WFI was 0.44 micrometer, compared with 2.07 after dilution in saline and 0.96 after dilution in saline with heat/shear stress. The initial percentage of droplets greater than 1 micrometer in diameter was 2.6%, compared with 42.8% after dilution in saline and 26.1% after dilution in saline with heat/shear stress. While Intralipid is a safe and clinically acceptable intravenous nutrition product, it is not useful as an injectable lubricant because this soybean oil emulsion shows large oil droplets and creaming following saline dilution/heat/shear stress.

Co-surfactant Saline Dilution/Heat/Shear Stress Tests

The percentage of large (greater than 1 micrometer) droplets, both initially and after saline dilution/heat/stress testing, was measured for emulsions having a series of co-surfactants. Dimyristoylphosphatidylglycerin (DMPG), a charged lipid, was added at 0.2%. Poloxamer 331, a lipophilic, non-ionic block copolymer, as added along with DMPG in another sample. Deoxycholate, a bile acid, was added at 0.4%. Poloxamer 331 was added along with deoxycholate in another sample. Intralipid was also tested.

The DMPG preparation initially had about 37% of droplets with a diameter greater than 1 micrometer, deoxycholate about 14%, poloxamer/deoxycholate and Intralipid about 3%, and poloxamer/DMPG about 2%. The failure of DMPG to cause smaller droplet size was unexpected since this lipid enhances the stabilizing electronegative surface charge on dispersed droplets.

After saline dilution/heat/stress testing, however, DMPG had about 37% of droplets with a diameter greater than 1 micrometer, poloxamer/deoxycholate about 32%, Intralipid and poloxamer/DMPG about 27% and deoxycholate about 15%. Thus, while some co-surfactants provide a finer initial droplet size distribution than deoxycholate, they provide much less protection against saline dilution/heat/shear stress. From studies such as these, we concluded that sodium deoxycholate is the most preferred co-surfactant.

While the preferred embodiment of the invention has been illustrated and described, it will be appreciated that various changes can be made therein without departing from the spirit and scope of the invention.

These corrections do not change the substance of the letter or the opinion reached with regards to patentability of the multi-vitamin S.E.T. compositions. The embodiments of the invention in which an exclusive property or privilege is claimed are defined as follows:

What is claimed is:

1. A medical lubricant oil emulsion comprising a mixture of:
    an oil;
    a surfactant;
    a co-surfactant;
    a pH buffer; wherein when said pH buffer is an amino acid buffer and said amino acid buffer has a concentration of less than 0.20 g/100 mL emulsion; and
    water.

2. A medical lubricant as recited in claim 1, wherein said oil comprises at least 60% mixed triglycerides of monounsaturated oleic acid, said surfactant is a phospholipid, said co-surfactant is a bile salt, and said pH buffer is an amino acid buffer having a concentration of less than 0.20g/100 mL emulsion.

3. A medical lubricant as recited in recited in claim 2, wherein said oil is a vegetable oil.

4. A medical lubricant as recited in claim 3, wherein said vegetable oil is selected from the group of refined oils consisting of almond oil, coconut oil, corn oil, cotton seed oil, marine oil, olive oil, palm kernel oil, peanut oil, safflower oil, sesame oil, soybean oil, sunflower oil, and physical or interesterified mixtures thereof.

5. A medical lubricant as recited in recited in claim 4, wherein said vegetable oil is purified olive oil comprised of at least 60% mixed triglycerides of mono-unsaturated oleic acid.

6. A medical lubricant as recited in claim 2, wherein said phospholipid is selected from the group consisting of soy bean and egg yolk phospholipids.

7. A medical lubricant as recited in claim 2, wherein said phospholipid is egg yolk phospholipid.

8. A medical lubricant as recited in claim 2, wherein said bile salt is selected from the group of salts of bile acids consisting of cholic acid, deoxycholic acid, glycocholic acid, taurocholic acid, and mixtures thereof.

9. A medical lubricant as recited in claim 8, wherein said bile salt is sodium deoxycholate.

10. A medical lubricant as recited in claim 2, wherein said amino acid buffer is selected from the group consisting of alanine, aspartic acid, glycine, histidine, isoleucine, leucine, methionine, phenylalanine, proline, serine, valine, and mixtures thereof.

11. A medical lubricant as recited in claim 10, wherein said amino acid buffer is L-histidine.

12. A medical lubricant as recited in claim 2, further comprising a cryogenic agent.

13. A medical lubricant as recited in claim 12, wherein said cryogenic agent is glycerin.

14. A medical lubricant as recited in claim 2, further comprising a heavy metal chelator.

15. A medical lubricant as recited in claim 14, wherein said chelator includes a physiologically acceptable salt of ethylenediamine tetracetic acid (EDTA).

16. A medical lubricant oil emulsion comprising:
    an oil;
    a phospholipid;
    a bile salt,
    a cryogenic agent;
    an amino acid buffer having a concentration of less than 0.20 g/100 mL emulsion; and
    water.

17. A medical lubricant as recited in claim 16, wherein said lipid emulsion has a mean droplet size less than about 5 micro meters.

18. A medical lubricant as recited in claim 16, wherein said lipid emulsion has a mean droplet size less than about 1 micro meter.

19. A medical lubricant as recited in claim 16, wherein said oil has a concentration of between about 5 and about 40 g/100 mL emulsion,
    said phospholipid includes egg yolk phospholipid and has a concentration of between about 0.3 and about 3 g/100 mL emulsion,
    said bile salt has a concentration of between about 0.04 and about 4.0 g/100 mL emulsion,
    said cryogenic agent is selected from the group consisting of refined propylene glycol and glycerin and has a concentration between about 1 and about 30 g/100 mL emulsion, and
    said amino acid buffer has a concentration of between about 0.01 and about 0.19 g/100 mL emulsion.

20. A medical lubricant as recited in claim 19, wherein said oil includes olive oil and has a concentration of between about 15 and about 25 g/100 mL emulsion,
    said phospholipid has a concentration of between about 0.6 and about 1.8 g/100 mL emulsion,
    said bile salt includes sodium deoxycholate and has a concentration of between about 0.2 and about 0.8 g/100 mL emulsion,
    said cryogenic agent includes glycerin and has a concentration between about 2 and about 20 g/100 mL emulsion, and
    said amino acid buffer includes L-histidine and has a concentration of between about 0.05 and 0.19 g/100 mL emulsion.

21. A medical lubricant oil emulsion comprising:
    refined olive oil;
    egg yolk phospholipid;
    sodium deoxycholate;
    glycerin;
    L-histidine having a concentration of less than 0.20 g/mL emulsion; and
    water for injection.

22. A medical lubricant as recited in claim 21, further comprising disodium EDTA and sodium hydroxide.

* * * * *

UNITED STATES PATENT AND TRADEMARK OFFICE
CERTIFICATE OF CORRECTION

PATENT NO. : 6,281,175 B1
DATED : August 28, 2001
INVENTOR(S) : R.T. Lyons et al.

It is certified that error appears in the above-identified patent and that said Letters Patent is hereby corrected as shown below:

Title page,
Item [73], Assignee, "Scimed" should read -- SCIMED --
Item [56], References Cited, FOREIGN PATENT DOCUMENTS, item 3, "7/1993" should read -- 8/1993 --

Column 14,
Line 58, "wherein when" should read -- wherein --

Column 15,
Line 1, delete the second occurrence of "recited in"
Line 9, delete the second occurrence of "recited in"

Signed and Sealed this

Seventh Day of May, 2002

Attest:

JAMES E. ROGAN
Attesting Officer    Director of the United States Patent and Trademark Office